United States Patent
Pinchuk et al.

(10) Patent No.: US 7,893,286 B2
(45) Date of Patent: Feb. 22, 2011

(54) METHOD FOR THE SYNTHESIS OF PHOSPHOLIPID ETHERS

(75) Inventors: Anatoly Pinchuk, Madison, WI (US); Jamey P. Weichert, Fitchburg, WI (US); Marc Longino, Verona, WI (US)

(73) Assignee: Cellectar, Inc., Madison, WI (US)

( * ) Notice: Subject to any disclaimer, the term of this patent is extended or adjusted under 35 U.S.C. 154(b) by 439 days.

(21) Appl. No.: 12/156,287

(22) Filed: May 30, 2008

(65) Prior Publication Data

US 2008/0312459 A1    Dec. 18, 2008

Related U.S. Application Data (60) Provisional application No. 60/932,748, filed on Jun. 1, 2007.

(51) Int. Cl.
*C07F 9/02* (2006.01)

(52) U.S. Cl. .................. 554/82; 424/1.65; 424/1.77; 424/1.85; 554/80; 554/84; 558/166; 558/169

(58) Field of Classification Search ............... 424/1.65, 424/1.77, 1.85; 554/80, 82, 84; 558/166, 558/169
See application file for complete search history.

(56) References Cited

U.S. PATENT DOCUMENTS

| | | |
|---|---|---|
| 4,925,649 A | 5/1990 | Counsell |
| 4,965,391 A | 10/1990 | Counsell |
| 5,087,721 A | 2/1992 | Counsell |
| 5,347,030 A | 9/1994 | Counsell |
| 5,369,097 A | 11/1994 | Salari |
| 5,795,561 A | 8/1998 | Counsell |
| 6,417,384 B1 | 7/2002 | Counsell |
| 2002/0065429 A1 | 5/2002 | Counsell |

FOREIGN PATENT DOCUMENTS

WO    WO 2005/084716 A2    9/2005

OTHER PUBLICATIONS

Arthur, G. et al., The Inhibition of Cell Signaling Pathways . . . R. Biochim Biophys Acta. (1998) 1390:85-102.
Becher, R. et al., Phase II Trial of Orally Administered Miltefosine . . . Onkologie-Germany (1993) 16; 1:11-15.
Berdel, W.E. et al., Daily Oral Miltefosine (Hexadecylphosphocholine) . . . Onkologie-Germany (1992) 15:238-242.
Clezy, P.S. et al., The Chemistry of Pyrrolic Compounds, Aust. J.Chem., (1969) 22:239-49.

(Continued)

*Primary Examiner*—Deborah D Carr
(74) *Attorney, Agent, or Firm*—Wood, Phillips, Katz, Clark & Mortimer

(57) ABSTRACT

Disclosed are improved methods for the synthesis of phospholipid ether analogs and alkyl phosphocholine analogs. The methods allow greater versatility of the reactants used and greater ease in synthesizing alkyl chains of varying length while affording reaction temperatures at room temperature or below. The methods disclosed herein provide reactants and conditions using alkyl halides and organozinc reagents and do not utilize Gringard reactions thus, allowing greater ease of their separation and purity of products. The PLE compounds synthesized by the methods disclosed herein can also be used for synthesizing high specific activity phospholipid ether (PLE) analogs, for use in treatment and diagnosis of cancer.

10 Claims, 2 Drawing Sheets

NM294

NM324

NM404

NM412

OTHER PUBLICATIONS

Counsell, R.E. et al., Tumor Visualization With a Radioiodinated Phospholipid . . . (1990) 31; 3:332-336.

Counsell, R.E. et al, Synthesis and Evluation of Radioiodinated Phospholipd Ether . . . Quart J. Nucl Med. (1997) 41(suppl 1):14-16.

Curley, SA et al., Radiofrequency Ablation of Unresectable Primary and Metastitic . . . Ann Surg. (1999) 230:1-8.

De Gramont, A. et al., Randomized Trial Comparing Monthly Low-Dose Leucovorin and . . . J. Clin. Oncol. (1997) 15:808-815.

Fong, Y. et al., Clinical Score for Predicting Recurrence After Hepatic Resection . . . Ann Surg. (1999) 230:309-318.

Giacchetti, S. et al., Phase III Multicenter Randomized Trial of Oxaliplatin Added . . . J. Clin. Oncol. (2000) 18:136-147.

Goud, T.V. et al., Synthesis of 8-Heteroatom-Substituted 4,4-Difluoro-4-Bora-3A, 4A-Diaza-S-Indacene Dyes (BODIPY), Tetrahedron 62 (2006) 5084-5091.

Greven, K. et al., Can Positron Emission Tomography Distinguish Tumor . . . Cancer Journal Scientifica American (1997) 3:353-357.

Ike, H. et al., Results of Agressive Resection of Lung Matastases From Colorectal Carcinoma . . . Dis colon Rectum (2002) 45:468-473.

Imboden, M. et al., The Level of MHC Class I Expression on Murine Adenocarcinoma Can Change . . . Cancer Res. (2001) 61:1500-1507.

Kallman, R. F. Rodent Tumor Models in Experimental Cancer Therapy Pergamon Press, New York, (1987) pp. 111-132.

Lencioni, R. et al., Percutaneous Radiofrequency Thermal Ablation of Liver Malignancies: Techniques . . . Abdom Imaging (2001) 26:345-360.

Liebeskind L.S. et al., Heteroaromatic Thioether—Bornic Acid Cross-Coupling . . . Dept. of Chem., Emory University, Organic Letters (2002) 4; 6:979-981.

Longino, M.A. et al., Tumor Selective Rentention of NM404—Involvement of Phospholipase D. Molecular Imaging (2004), 3(3).

Maier, O. et al., Fluorescent Lipid Probes: Some Properties and Application (A Review) Chemistry and Physics of Lipids 116 (2002) 3-18.

Mayr, N.A. et al., Method and Timing of Tumor Volume Measurement for Outcome . . . Int. J. of Rad., Oncol., Bio., Phys. (2002) 52; 1:14-22.

Meta-Analysis:Modulation of Fluorouracil by . . . Advanced Colorectal Cancer Meta-Analysis Project. J. clin. Oncol. (1992) 10:896-903.

Moser, A.R. et al., Specificity of NM404 for Hyperplasia Versus Neoplasia in the . . . Online Aug. 15-18, 2003 Presentation No. 305.

O'Dwyer, P.J. et al., Follow-Up of Stage B and C Colorectal Cancer in the United States and . . . Seminars in Onology (2001) 28:Suppl-9.

Penna, C., et al., Colorectal Metastasis (Liver and Lung), Surg. clin. North Amer. (2002) 82:1075-10xi.

Pickhardt, P.J. et al., Computed Tomographic Virtual Colonoscopy to Screen for Colorectal . . . NE J. Med. (2003) 349; 23:2191-2200.

Plotzke, K.P. et. al., Selective Localization of a Radioiodinated Phospholipid Ether Analog in Human Tumor . . . J. Nucl. Med. (1993) 34(5):787-792.

Plotzke, K.P. et. al., Selective Localization of Radioiodinated Alkylphosphocholine . . . Int. J. RadPart B, Nucl. Med. & Biology. (1992) 19(7):765-773.

Rampy, M.A. et al., Biological Disposition and Imaging of a Radioiodinated Alkylphosphocholine in Two Rodent . . . J. Nucl. Med. (1996) 37(9):1540-1545.

Rampy, M.A. et al., Synthesis and Biological Evaluation of Radioiodinated Phospholipid Ether Stereoisomers, J. Med. Chem. (1995) 38:3156-3162.

Saltz, L.B. et al., Irinotecan Plus Fluorouracil and Leucovorin for Metastiatic Colorectal Cancer . . . , N. Engl. J. Med. (2000) 343:905-91.

Snyder, F. et al., Alkyl and Alk-1-Enyl Ethers of Glycerol in Lipids From Normal and Neoplastic Human Tissues, Cancer Research. (1969) 29:251-257.

Snyder, F. et al., Occurrence and Nature of O-Alkyl and O-Alkyl-L-Enyl Moieties of Glycerol in Lipids of Morris . . . Biochem Biophys Acta. (1969) 176:502-510.

Solbiati, L. et al., Percutaneous Radio-Frequency Ablation of Hepatic Metastases From Colorectal Cancer: Long-Term . . . Radiology (2001) 221:159-166.

Stahl, A. et al., PET/CT Molecular Imaging in Abdominal Oncology, Abdominal Imaging (2004) 29:3(388-397).

Terwogt, J.M.M. et al., Phase II Trial of Topically Applied Miltefosine Solution in Optients With Skin-Metastasized . . . British J. of Cancer (1999) 79:1158-1161.

Wagner, R. et al., Boron-Dipyrromethene Dyes for Incorporation in Synthetic Multi-Pigment Light-Harvesting Arrays, Pure & Appl. Chem., (1996) 68; 7:1373-1380.

Wang, H.E. et al., Molecular Imaging With 123I-FIAU, 18F-FUdR, 18F-FET, and 18F-FDG for Monitoring Herpes . . . J. of Nuclear Med. (Jul. 2006) 47; 7:1161-1171.

Weber, S.M. et al., Interleukin-1 Gene Transfer Results in CD8-Dependent Regression of Murine CT26 Liver Tumors, Ann. Surg. Oncol. (1999) 6:186-194.

Weichert, J.P. et al., Initial Clinical Imagining Results With NM404 in Non-Small Cell Lung Cancer, Molecular Imaging Online (2004) 3; 3:269-270.

Wichmann, M.W. et al., The Colorectal Cancer Study Group. Carcinoembryonic Antigen for the Detection . . . Anticancer Research (2000) 20:4953-4955.

Zasadny, K.R. et al., Predicted Dosimetry for I-131-NM404, A Phospholipid Ether Agent for Tumor Imaging and Possible Therapy, J Nucl Med. (1999) 40(5):39P.

Quon, A. et al., "Flying Through" and "Flying Around" A PET/CT Scan: Pilot Study . . . J. of Nuclear Med. (Jul. 2006) 47; 7:1081-1087.

Sik, M.D. et al., Neoplastic Transformation and Tumorrigensis Associated With Overexpress . . . Database Biosis(Online) (Oct. 2001) XP002365147 Database No. PREV200100523916.

Hirokazu O. et al., Increased Activity and Expression of Phospholipase D2 in Human . . . Database Biosis (Online) (2003) XP002365146 Database No. PREV00300566956.

Dong-Young, N. et al., Overexpression of Phospholipase D1 in Human Breast Cancer Tissues, Database Biosis (Online) (Dec. 2000) XP002365186 Database No. PREV200100047408.

Weichert, J. et al., Specificity of NM404 for Hyperplasia versus Neoplasia in the APC . . . Oasis—Online Abstrct Submission and Invitation System, 1996-2007.

Weichert JP et al "Evaluation of 125I-NM404 in a Spontaneous Murine Pancreatic Adenocarcinoma . . . ", Aug. 2003, 2nd Annual Meeting of the Society of Molecular Imaging, San.

Weichert J. et al., Radioiodination Via Isotope Exchange in Pivalic Acid, Appl. Radiat Isot (1986) vol. 37, No. 8, 907-913.

Weichert J. et al., Polyiodinated Triglyceride Analogs as Potential Computed Tomography Imaging Agents for the Liver, J Med Chem (1995) 38, 636-646.

Pinchuk A. et al., Synthesis and Structure-Activity Relationship Effects on the Tumor Avidity of Radioiodinated Phospholipid Ether Analogues, J Med Chem (2006), 49, 2155-2165.

METHOD FOR THE SYNTHESIS OF PHOSPHOLIPID ETHERS

FIELD OF THE INVENTION

The present invention relates to methods for the synthesis of phospholipid ether analogs. Specifically, the invention provides a more versatile, less time consuming and less dangerous method for the synthesis of phospholipid ether analogs for use in cancer therapy.

BACKGROUND

Previously, the inventors have identified and reported the use of a series of novel phospholipid ether (PLE) compounds demonstrating useful tumor specificity. See, e.g., U.S. patent application Ser. Nos. 10/906,687, 11/177,749, 11/316,620, 11/382,645, all of which are herein incorporated by reference in their entirety for all purposes. While such PLE compounds are remarkably specific in targeting cancer yet versatile in the array of cancer types they target, the synthesis of PLE compounds is a multi-step procedure that requires the use of hazardous reagents and has limited versatility in terms of the starting reactants used in synthesizing alkyl chain length of the PLE tail.

Accordingly it is desirable to develop a more concise and less dangerous synthesis that also increases the versatility of the reactants used.

SUMMARY OF THE INVENTION

Disclosed are improved methods for the synthesis of phospholipid ether analogs and alkyl phosphocholine analogs. The methods allow greater versatility of the reactants used and greater ease in synthesizing alkyl chains of varying length while affording reaction temperatures and at room temperature or below. The methods disclosed herein provide reactants and conditions using alkyl halides and organozinc reagents and do not utilize Gringard reactions thus, allowing greater ease of their separation and purity of products. The PLE compounds synthesized by the methods disclosed herein can also be used for synthesizing high specific activity phospholipid ether (PLE) analogs, for use in treatment and diagnosis of cancer.

Therefore, in one preferred embodiment, the invention provides an improved method for synthesizing PLE analogs useful for the treatment of primary cancer, secondary cancer, recurrence of cancer, radiation insensitive cancer, chemo insensitive cancer or metastasis of cancer in a subject.

Further, in some preferred embodiments of the invention, the cancer is selected from the group consisting of: lung cancer, adrenal cancer, melanoma, colon cancer, colorectal cancer, ovarian cancer, prostate cancer, liver cancer, subcutaneous cancer, squamous cell cancer, adenocarcinoma, intestinal cancer, hepatocellular carcinoma, retinoblastoma, cervical cancer, glioma, breast cancer, pancreatic cancer, carcinosarcoma, hepatoma and carcinosarcoma.

Therefore, in one exemplary embodiment, the invention provides a method of synthesizing a phospholipid ether (PLE) analog or an alkyl phosphocholine (APC) analog comprising the cross-coupling of an organo zinc reagent with an alkyl halide reagent comprising the steps of:
a) coupling an alkyl organo metallic with an alkyl iodide in the presence of an Ni(II)-Pybox or Pd-PEPPSI catalyst;
b) attaching an iodophenyl group in the presence of an Ni(II)-Pybox catalyst to yield an iodophenyl alcohol; and
c) converting the iodophenyl alcohol to an iodophenyl phosphocholine using an ethylene chlorophosphate and trimethylamine; wherein an alkyl phospholipid or phospholipid ether is synthesized.

In these methods, the phospholipid ether analog has the formula I:

where X is selected from the group consisting of radioactive isotopes of halogen; n is an integer between 8 and 30; and Y is selected from the group comprising $NH_2$, $NR_2$, and $NR_3$, wherein R is an alkyl or arylalkyl substituent or the compound shown in formula II:

where X is a radioactive isotope of halogen; n is an integer between 8 and 30; Y is selected from the group consisting of H, OH, COOH, COOR and OR, and Z is selected from the group consisting of $NH_2$, $NR_2$, and $NR_3$, wherein R is an alkyl or arylalkyl substituent. In some version of the invention, X is selected from the group of radioactive halogen isotopes consisting of $^{18}F$, $^{36}Cl$, $^{10}Br$, $^{76}Br$, $^{77}Br$, $^{82}Br$, $^{122}I$, $^{123}I$, $^{124}I$, $^{125}I$, $^{131}I$, $^{211}At$ and combinations thereof. In some versions, synthesis of the PLE analog alkyl chain is described as: $IPhC_1 + C_{11} + C_6 = IPhC_{18}$, $C_6 + C_{11} + IPhC_1 = IPhC_{18}$, $C_{16} + IPhC_2 = IPhC_{18}$.

In other exemplary embodiments, the invention uses a catalyst having the structure shown in formula III:

wherein R is selected from the group consisting of: i-Pr: i-Pr-Pybox, s-Bu: s-Bu-Pybox, Ph: Ph-Pybox and H: Pybox; or the compound shown in formula IV:

IV

In yet another preferred embodiment, the invention includes a method of synthesizing high specific activity phospholipid ether (PLE) analog, comprising the step of: (a) coupling an ester of diboron with the PLE analog in the presence a catalyst to result in a boronic acid or pinacolboronate ester analog; (b) optionally esterifying the boronic acid analog of the PLE analog with pinacol to result in the pinacol ester analog to step (a); and (c) reacting the boronic acid or pinacolboronate analog of step (a) or (b) with sodium halide, in the presence of a chloramine-T, dichloramine-T, chloramine-B, dichloramine-B, iodogen, N-chlorosuccinimide, NaOCl, hydrogen peroxide or peroxidase enzyme to result in a high specific activity PLE analog. In some preferred embodiments, the coupling reaction of step (a) is carried with methanol as a solvent at temperature of about 15-70° C. in the presence of a Pd catalyst (formula IV).

In some preferred embodiments, the invention includes an intermediate in the synthesis having the structure shown in formula V:

V

Other objects, features and advantages of the present invention will become apparent from the following detailed description. It should be understood, however, that the detailed description and the specific examples, while indicating exemplary embodiments of the invention, are given by way of illustration only, since various changes and modifications within the spirit and scope of the invention will become apparent to those skilled in the art from the detailed description.

GENERAL DESCRIPTION OF THE INVENTION

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to optical isomers and analogs, structural isomers and analogs, conformational isomers and analogs, and the like. In one embodiment, this invention encompasses the use of different optical isomers of an anti-tumor compound shown in Formula I. It will be appreciated by those skilled in the art that the anti-tumor compounds useful in the present invention may contain at least one chiral center. Accordingly, the compounds used in the methods of the present invention may exist in, and be isolated in, optically-active or racemic forms. Some compounds may also exhibit polymorphism.

It is to be understood that the present invention may encompass the use of any racemic, optically-active, polymorphic, or stereroisomeric form, or mixtures thereof, which form possesses properties useful in the treatment of tumor-related conditions described and claimed herein. In one embodiment, the anti-tumor compounds may include pure (R)-isomers. In another embodiment, the anti-tumor compounds may include pure (S)-isomers. In another embodiment, the compounds may include a mixture of the (R) and the (S) isomers. In another embodiment, the compounds may include a racemic mixture comprising both (R) and (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes methods utilizing derivatives of the anti-tumor compounds. The term "derivatives" includes but is not limited to ether derivatives, acid derivatives, amide derivatives, ester derivatives and the like. In addition, this invention further includes methods utilizing hydrates of the anti-tumor compounds. The term "hydrate" includes but is not limited to hemihydrate, monohydrate, dihydrate, trihydrate and the like.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, "pharmaceutical composition" means therapeutically effective amounts of the anti-tumor compound having radioactivity together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of disease (e.g., pancreatic cancer, breast cancer, lung cancer etc.); and (b) the reversal or stabilization of such disease. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween (Polysorbate) 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski A et al. *Cancer Treat. Rep.* 1981; 65: 1077-1081; Newmark J et al. *J. Appl. Biochem.* 1982; 4: 185-189; Katre N et al. *Proc. Natl. Acad. Sci. U.S.A.* 1987; 84: 1487-1491.). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Generally, phospholipid ether compounds and especially NM404 are promising new tumor-selective diagnostic imaging agents to monitor the treatment response of several tumor treatment modalities.

As used herein "alkyl" group refers to a straight chain, branched or cyclic, saturated or unsaturated aliphatic hydrocarbons. The alkyl group has 1-16 carbons, and may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. A "hydroxy" group refers to an OH group. An "alkoxy" group refers to an —O-alkyl group wherein alkyl is as defined above. A "thio" group refers to an —SH group. A "thioalkyl" group refers to an —SR group wherein R is alkyl as defined above. An "amino" group refers to an —NH$_2$ group. An "alkylamino" group refers to an —NHR group wherein R is alkyl is as defined above. A "dialkylamino" group refers to an —NRR' group wherein R and R' are all as defined above. An "amido" group refers to an —CONH$_2$. An "alkylamido" group refers to an —CONHR group wherein R is alkyl is as defined above. A "dialkylamido" group refers to an —CONRR' group wherein R and R' are alkyl as defined above. A "nitro" group refers to an NO$_2$ group. A "carboxyl" group refers to a COOH group.

As used herein, "aryl" includes both carbocyclic and heterocyclic aromatic rings, both monocyclic and fused polycyclic, where the aromatic rings can be 5-or 6-membered rings. Representative monocyclic aryl groups include, but are not limited to, phenyl, furanyl, pyrrolyl, thienyl, pyridinyl, pyrimidinyl, oxazolyl, isoxazolyl, pyrazolyl, imidazolyl, thiazolyl, isothiazolyl and the like. Fused polycyclic aryl groups are those aromatic groups that include a 5-or 6-membered aromatic or heteroaromatic ring as one or more rings in a fused ring system. Representative fused polycyclic aryl groups include naphthalene, anthracene, indolizine, indole, isoindole, benzofuran, benzothiophene, indazole, benzimidazole, benzthiazole, purine, quinoline, isoquinoline, cinnoline, phthalazine, quinazoline, quinoxaline, 1,8-naphthyridine, pteridine, carbazole, acridine, phenazine, phenothiazine, phenoxazine, and azulene. Further, as used herein "arylalkyl" refers to moieties, such as benzyl, wherein an aromatic is linked to an alkyl group which is linked to the indicated position in the PLE compound.

Preferred Embodiments

Generally, this invention provides for molecules and methods for the treatment of cancer based on the design of carrier molecules which are capable of selectively delivering a diagnostic or therapeutic probe to the desired target tissue capitalizing on the unique biochemical or pharmacological properties of phospholipid ethers (PLE). PLE display a high degree of tissue or tumor selectivity, in particular very long and persistent cancer-selective retention.

Phospholipids are the major lipid component of cell membranes. Ether phospholipids are a minor phospholipid subclass differing by having an ether linkage at the C-1 carbon of the glycerol backbone rather than the normal ester bond. Assessment of this new class of cancer treatments in several animal tumor models provided by the inventors revealed that NM404 (18-[4-Iodophenyl]-octadecyl phosphocholine) accumulates in primary and/or metastatic tumors. Alkyl phosphocholines (APC), for example, hexadecylphosphocholine (HPC), are another subclass of compounds that have shown antineoplastic activity.

Figure 1:
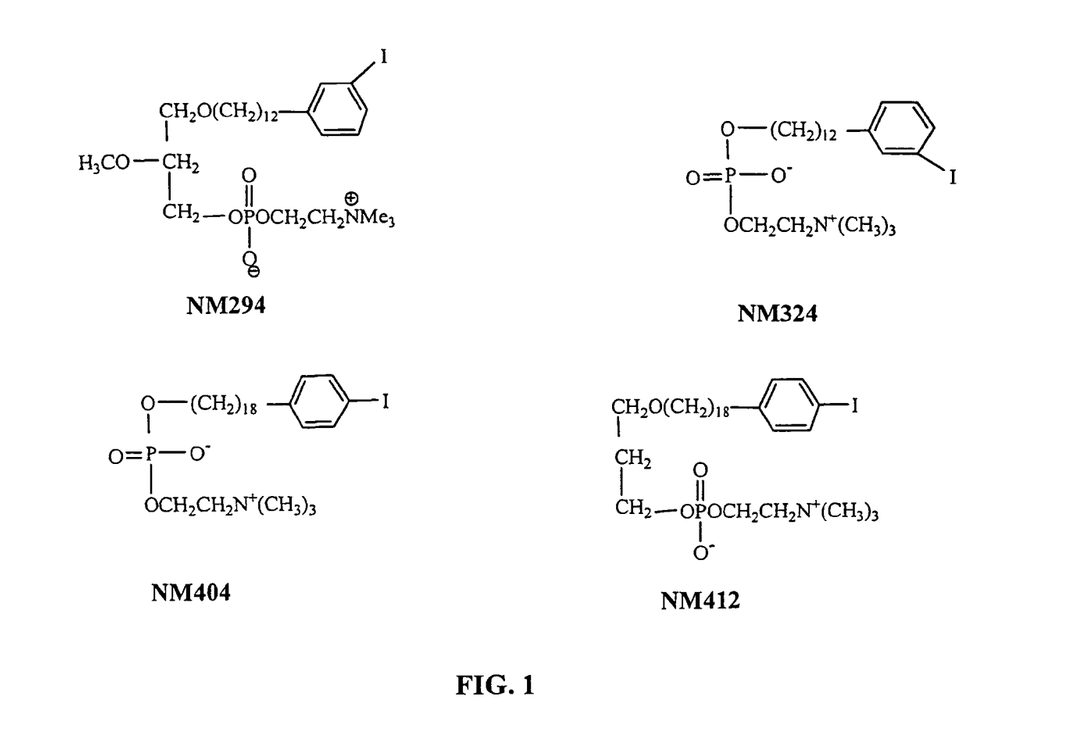
FIG. 1, Structures of some PLE analogs of the invention.
Figure 2:
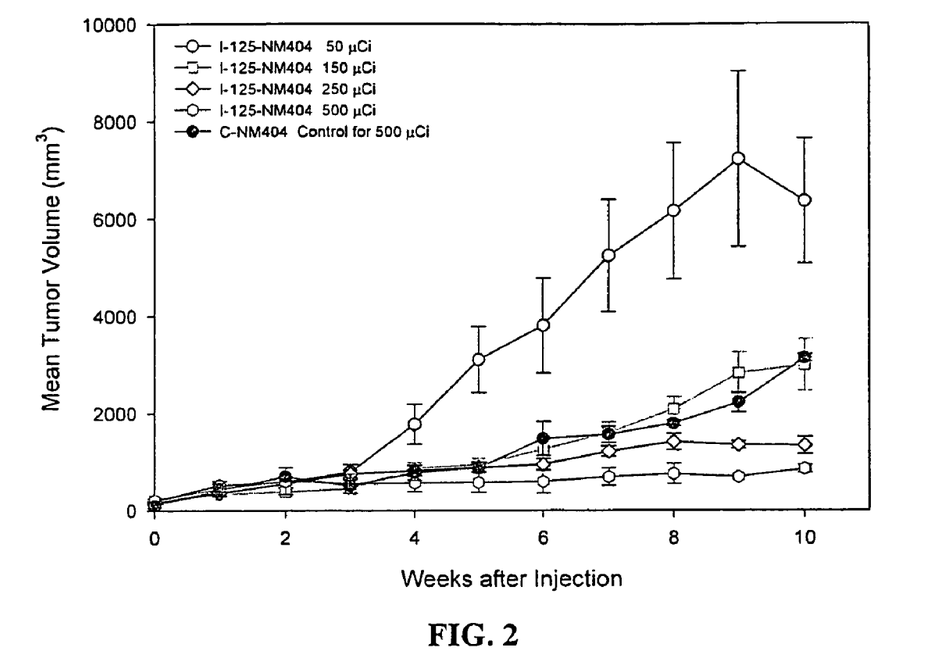
FIG. 2, illustrates antitumor effect of single-dose treatment with $^{125}$I-125-NM404 at doses of 50 (⊛), 150 (□), 250 (◇) and 500 (○) μCi in SCID mice bearing A549 human non-small cell lung cancer xenografts. In this figure, control animals show rapidly growing tumors over the 10-week assessment period. This confirms that the compound itself C-NM404 has no substantial effect on tumor growth. The 50 and 150 μCi dose groups did not show any difference when compared to control animals, hence these seem to be ineffective dose levels in this animal model. However, the 250 and 500 μCi dose groups show a substantial and prolonged treatment effect. The results show a dose-linear effect of $^{125}$I-NM404 on tumor volume. ♦ Control, C-NM404.
Figure 3:
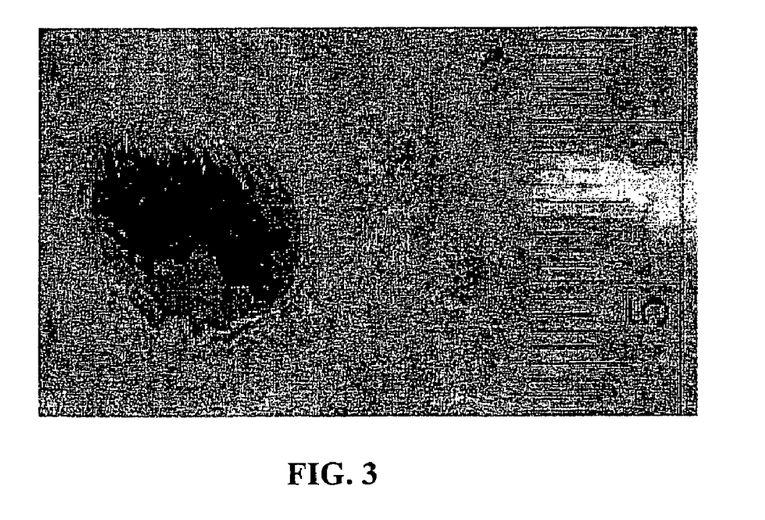
FIG. 3 is an image showing one of the tumor-bearing animals treated with 250 μCi of $^{125}$I-NM404 at 4 weeks following injection. The hair above the tumor has fallen off, apparently due to the significant accumulation of radioactivity in the tumor. Additionally, the surface of the tumors appears "caved in" and shows darker areas, presumably from hemorrhage and necrosis. The figure shows the effect of $^{125}$I-NM404 on the tumor. Although tumor size (outer dimensions) may not decrease, $^{125}$I-NM404 causes central necrosis. The measurement method for determining outer tumor dimensions may have underestimated tumor volume response following dosing with $^{125}$I-NM404.

The inventors have shown that $^{125}$I-labeled NM404 is an effective tumor therapy treatment following single injection and fractionated dosing. FIG. 2 summarizes investigations into the efficacy of $^{125}$I-NM404 treatment. These investigations provided assessments of tumor volume were made until 10 weeks post-injection or until no animal in the control group is alive, whatever came first. Summarizing the results, control animals show rapidly growing tumors over the 10-week assessment period. This confirms that the unlabeled compound itself NM404 has no substantial effect on tumors growth. The 50 μCi dose group did not show any difference to control animals, hence these seem to be ineffective dose levels in this animal model. However, the 150, 250 and 500 μCi dose groups show a substantial and prolonged treatment effect. Tumor volumes are stable and same tumors appear "collapsed" (the tumor surface has caved in). Additionally, FIG. 3 illustrates that hair above the tumors fell off confirming substantial accumulation of radioactivity in these tumors. The results show a dose-linear effect of $^{125}$I-NM404 on tumor volume.

Thus, in one exemplary embodiment, the present invention provides an improved method for the synthesis of PLE analogs useful for the treatment of primary cancer, secondary cancer, recurrence of cancer, radiation insensitive cancer, chemo insensitive cancer or metastasis of cancer in a subject.

As previously described in, for example, U.S. patent application Ser. Nos. 10/906,687 and 11/177,749, the compounds described herein may be used in various cancers and cell types including but not limited to lung cancer, adrenal cancer, melanoma, colon cancer, colorectal cancer, ovarian cancer, prostate cancer, liver cancer, subcutaneous cancer, squamous cell cancer, adenocarcinoma, intestinal cancer, hepatocellular carcinoma, retinoblastoma, cervical cancer, glioma, breast cancer, pancreatic cancer, carcinosarcoma, hepatoma and carcinosarcoma.

Therefore, in one exemplary embodiment, the invention provides a method of synthesizing a phospholipid ether (PLE) analog or an alkyl phosphocholine (APC) analog comprising by the cross-coupling of an organo zinc reagent with an alkyl halide reagent comprising the steps of:

a) coupling an alkyl organo metallic with an alkyl iodide in the presence of an Ni(II)-Pybox or Pd-PEPPSI catalyst;

b) attaching an iodophenyl group in the presence of an Ni(II)-Pybox catalyst to yield an iodophenyl alcohol; and c) converting the iodophenyl alcohol to an iodophenyl phosphocholine using an ethylene chlorophosphate and trimethylamine; wherein an alkyl phospholipid or phospholipid ether is synthesized.

In these methods, the phospholipid ether analog has the formula I:

where X is selected from the group consisting of radioactive isotopes of halogen; n is an integer between 8 and 30; and Y is selected from the group comprising NH$_2$, NR$_2$, and NR$_3$, wherein R is an alkyl or arylalkyl substituent or the compound shown in formula II:

II where X is a radioactive isotope of halogen; n is an integer between 8 and 30; Y is selected from the group consisting of H, OH, COOH, COOR and OR, and Z is selected from the group consisting of $NH_2$, $NR_2$, and $NR_3$, wherein R is an alkyl or arylalkyl substituent. In some version of the invention, X is selected from the group of radioactive halogen isotopes consisting of $^{18}F$, $^{36}Cl$, $^{10}Br$, $^{76}Br$, $^{77}Br$, $^{82}Br$, $^{122}I$, $^{123}I$, $^{124}I$, $^{125}I$, $^{131}I$, $^{211}At$ and combinations thereof.

In some versions, synthesis of the PLE analog alkyl chain is described as: $IPhC_1+C_{11}+C_6=IPhC_{18}$, $C_6+C_{11}+IPhC_1=IPhC_{18}$ and $C_{16}+IPhC_2=IPhC_{18}$.

In other exemplary embodiments, the invention uses a catalyst having the structure shown in formula III:

III wherein R is selected from the group consisting of: i-Pr: i-Pr-Pybox, s-Bu: s-Bu-Pybox, Ph: Ph-Pybox and H: Pybox; or the compound shown in formula IV:

IV

In yet another preferred embodiment, the invention includes a method of synthesizing high specific activity phospholipid ether (PLE) or alkyl phosphocholine (APC) analog, comprising the step of: (a) coupling an ester of diboron with the PLE or APC analog in the presence a catalyst to result in a boronic acid or pinacolboronate ester analog; (b) optionally esterifying the boronic acid analog of the PLE analog with pinacol to result in the pinacol ester analog to step (a); and (c) reacting the boronic acid or pinacolboronate analog of step (a) or (b) with sodium halide, in the presence of a chloramine-T, dichloramine-T, chloramine-B, dichloramine-B, iodogen, N-chlorosuccinimide, NaOCl, hydrogen peroxide or peroxidase enzyme to result in a high specific activity PLE analog. In some preferred embodiments, the coupling reaction of step (a) is carried with methanol as a solvent at temperature of about 15-70° C. in the presence of a Pd catalyst (formula IV).

In some preferred embodiments, the invention includes an intermediate in the synthesis having the structure shown in formula V:

V

EXAMPLE 1

Improved Synthesis of Long Chain ω-(p-Iodophenyl)alkyl Alcohols and Corresponding Phospholipid Ethers and Alkyl Phosphocholines Including NM404

The catalyst (Formula III) is a Ni(II) complex of 2,6-bis-(4-isopropyl-2-oxazolin-2-yl)-pyridine (1-Pr-Pybox) 71 or 2,6-bis-(4-sec-butyl-2-oxazolin-2-yl)-pyridine (s-Bu-Pybox) 72 or 2,6-bis-(4-phenyl-2-oxazolin-2-yl)-pyridine (Ph-Pybox) 73 or pybox (H-Pybox) 74 or 2,6-bis-(4-phenylethyl-2-oxazolin-2-yl)-pyridine ($BnCH_2$-Pybox) 75. The cross-coupling reaction can be performed at 0° C. or room temperature.

III

71, R = i-Pr: i-Pr-Pybox
72, R = s-Bu: s-Bu-Pybox
73, R = Ph: Ph-Pybox
74, R = H: Pybox
75, R = $BnCH_2$: $BnCH_2$-Pybox In some preferred embodiments, the invention includes an intermediate in the synthesis having the structure shown in formula V:

V

In this embodiment, M is selected from the group consisting of Li, Na, K, Cs and Rb.

This method allows to synthesize 18-(p-iodophenyl)octadecanol 12 from various commercial precursors. One approach is shown in Scheme I. In the first step, organozinc reagent 33 obtained from 11-bromoundecyl acetate is coupled with p-iodobenzyl bromide 5 to produce 12-(p-iodophenyl)dodecyl acetate 34. Hydrolysis of the acetate 34 and conversion of 12-(p-iodophenyl)dodecanol 7 into iodide 35 provides a coupling partner for the next reaction with organozinc reagent 36. Final coupling product 37 is an ester which is converted into 18-(p-iodophenyl)octadecanol 12 in a two-steps process. In a summary, the chain elongation process can be abbreviated as $IPhC_1+C_{11}+C_6=IPhC_{18}$.

SCHEME I:

Methods

Synthesis of 12-(p-Iodophenyl)dodecyl acetate (34).

Zinc powder (146 mg, 2.25 mmol) was heated to 70° C. in a 10-ml Schlenk tube under high vacuum for 30 min. After back-filling with nitrogen, DMA (2 ml) and iodine (19 mg, 0.08 mmol) were added, and the resulting mixture was stirred until the color of iodine had faded. Then, neat 11-bromoundecyl acetate (440 mg, 1.5 mmol) was added. The reaction mixture was stirred for 12 h at 70° C., cooled to the room temperature, excess of zinc was allowed to settle, and the clear gray-colored solution of organozinc reagent was transferred into a 5-ml round bottom flask via cannula.

In a 10-ml flask, $NiCl_2$.glyme (40 mg, 0.18 mmol) and (R)-(i-Pr)-Pybox (or (S)-(i-Pr)-Pybox) (68 mg, 0.225 mmol) were dissolved in DMA (1.5 ml) then the solution of p-iodobenzyl bromide 5 in THF (0.7 ml) was added. After stirring for 10 min at 0° C., organozinc reagent 33 was added. The mixture was stirred at 0° C. for 30 min and at room temperature for 12 h. The reaction mixture was quenched with $NH_4Cl$ solution, extracted with EtOAc, the extract was dried over $Na_2SO_4$ and evaporated. Residual material was chromatographed on silica gel in hexane-ether (98:2) to give the product, 408 mg (63%).

Using catalyst composed of $Ni(COD)_2$ (0.05 eq) and (i-Pr)-Pybox (0.1 eq) in this procedure resulted in 72% yield.

Synthesis of 12-(p-Iodophenyl)dodecanol (7).

12-(p-Iodophenyl)dodecyl acetate 34 (872 mg, 2.03 mol) was dissolved in THF (4 ml) and MeOH (4 ml) mixture, and a solution of NaOH (325 mg, 8.11 mmol) in $H_2O$ (1 ml) was added. The mixture was stirred at room temperature for 5 h, quenched with 1 N HCl to pH 7, diluted with $NaHCO_3$ solution and extracted with EtOAc. The extract was dried over $Na_2SO_4$ and the solvent was evaporated. Silica gel chromatography of the residue in hexane-ethyl acetate (95:5, 90:10) yielded the product (682 mg, 87%) as a white solid.

Synthesis of 12-(p-Iodophenyl)dodecyl iodide (35).

12-(β-Iodophenyl)dodecanol 7 (676 mg, 1.74 mmol), $Ph_3P$ (548 mg, 2.09 mmol) and imidazole (196 mg, 2.87 mmol) were dissolved in the mixture of $CH_2Cl_2$ (8 ml) and benzene (5 ml) and cooled to 0° C. Solid $I_2$ (530 mg, 2.09 mmol) was added. The mixture was stirred at 0° C. for 30 min, and at room temperature for 1 h. The reaction was quenched by the addition of MeOH (1 ml), diluted with $NaHCO_3$ solution and extracted with EtOAc. Chromatography in hexane-$CH_2Cl_2$ (98:2) gave the product as a white solid, 802 mg (93%).

Synthesis of Ethyl 18-(p-iodophenyl)octadecanoate (37) from (35).

Zinc powder (156 mg, 2.4 mmol) was heated to 70° C. in a 10-ml Schlenk tube under high vacuum for 30 min. After back-filling with nitrogen, DMA (1.5 ml) and iodine (20 mg, 0.08 mmol) were added. After the color of iodine had disappeared, neat ethyl 6-bromohexanoate (0.29 ml, 1.61 mmol) was added. The mixture was stirred at 70° C. for 10 h, cooled to the room temperature, zinc excess was allowed to settle, and the organozinc solution was transferred via cannula into a storage vessel. In a 10-ml flask, $NiCl_2$-glyme (18 mg, 0.08 mmol) and (R)-(i-Pr)-Pybox (or (S)-(i-Pr)-Pybox) (31 mg, 0.1 mmol) were dissolved in DMA (2.5 ml) and THF (0.5 ml), cooled to 0° C. and the organozinc reagent 36 was added via cannula. The reaction mixture was stirred at 0° C. for 10 h and at room temperature for 24 h, then quenched with $NH_4Cl$ solution and extracted with EtOAc. The organic extract was dried over $Na_2SO_4$ and evaporated. The crude product was purified by silica gel chromatography in hexane-ether (98:2, 97:3) to afford the product, 281 mg (68%).

Using catalyst composed of $Ni(COD)_2$ (0.04 eq) and (s-Bu)-Pybox (0.08 eq) and DMA as a solvent in this procedure resulted in 36% yield.

Synthesis of 18-(p-Iodophenyl)octadecanol (12) from (37).

Ethyl 18-(p-iodophenyl)octadecanoate 37 (270 mg, 0.52 mmol) was dissolved in THF (3 ml) and MeOH (3 ml) to which a solution of NaOH (300 mg, 7.5 mmol) in $H_2O$ (0.7 ml) was added. Reaction mixture was stirred at room temperature for 4 h, quenched with 8 ml of 1 N HCl and extracted with EtOAc. The organic extract was washed with NaCl solution twice, dried over $Na_2SO_4$ and evaporated to give 254 mg of the crude material.

The crude material was dissolved in THF (1 ml) and $BH_3$.THF (3 ml, 3 mmol) was added at 0° C. The reaction mixture was maintained at +4° C. overnight, and then quenched with $H_2O$ at 0° C. The mixture was extracted with EtOAc, extract was dried over $Na_2SO_4$ and evaporated. The residue was purified by silica gel chromatography in hexane-EtOAc (95:5, 90:10) to give the product, 232 mg (94%).

Another possibility, based on different cross-coupling partners is shown in Scheme II. The chain elongation sequence is $C_6+C_{11}+IPhC_1=IPhC_{18}$. First coupling between THP ether of 6-iodohexanol 38 and $C_{11}$ organozinc reagent 33 produces $C_{17}$ fragment 39. Removal of THP protecting group, conversion of intermediate alcohol into bromide 40 followed by formation of organozinc 41 produces another partner for cross-coupling reaction. Ni(II)-catalyzed coupling of organozinc 41 with p-iodobenzyl bromide 5 completes the chain elongation. Hydrolysis of the acetate 42 gives 18-(p-iodophenyl)octadecanol 12.

SCHEME II:

Methods

Synthesis of Tetrahydro-2-(17-acetoxyheptadecyloxy)-2H-pyran (39).

In a 10-ml Schlenk tube, zinc powder (98 mg, 1.5 mmol) was dried at 70° C. under high vacuum for 30 min. After back-filling with nitrogen, DMI (1 ml) and iodine (13 mg, 0.05 mmol) were added. The mixture was stirred until disappearance of the iodine color, after which neat 11-bromoundecyl acetate (293 mg, 1 mmol) was added. The tube was sealed, and the mixture was stirred at 70° C. for 12 h, cooled to the room temperature and zinc excess was allowed to settle. In a 5-ml flask, NiCl$_2$-glyme (17 mg, 0.08 mmol) and (R)-(i-Pr)-Pybox (or (S)-(i-Pr)-Pybox) (30 mg, 0.1 mmol) were dissolved in DMI (1 ml) and THF (0.3 ml), then neat I(CH$_2$)$_6$OTHP 38 (240 mg, 0.77 mmol) was added followed by addition of the organozinc solution 33 via cannula. The reaction mixture was stirred at room temperature for 14 h, quenched with NH$_4$Cl and extracted with EtOAc. The organic extract was dried over Na$_2$SO$_4$ and concentrated by solvent evaporation. Chromatography in hexane-ethyl ether (15:1, 10:1) gave the product, 212 mg (69%).

Synthesis of 17-Acetoxy-heptadecyl bromide (40).

1). THP ether 39 (1.207 g, 3.03 mmol) was dissolved in 95% EtOH (12 ml) and PPTS (76 mg, 0.3 mmol) was added. The mixture was stirred at 55° C. for 4 h, cooled to room temperature and diluted with EtOAc. This mixture was washed with H$_2$O three times, the organic phase was dried over Na$_2$SO$_4$ and evaporated. The residue was chromatographed on silica gel to give 864 mg (91%) of 17-acetoxy-heptadecanol.

2) Intermediate 17-acetoxy-heptadecanol (220 mg, 0.7 mmol) and CBr$_4$ (302 mg, 0.91 mmol) were dissolved in CH$_2$Cl$_2$ (2 ml) and a solution of Ph$_3$P (238 mg, 0.91 mmol) in CH$_2$Cl$_2$ (1.5 ml) was added via cannula at 0° C. The reaction was stirred at 0° C. for 2 h and then quenched with MeOH (0.3 ml), stirred for additional 10 min at room temperature, diluted with EtOAc and washed with aqueous NaHCO$_3$ solution. The organic extract was dried over Na$_2$SO$_4$ and evaporated. Silica gel chromatography in hexane-EtOAc (99:1, 95:5) provided 261 mg (99%) of 17-acetoxy-heptadecyl bromide (40).

Synthesis of 17-Acetoxy-heptadecyl iodide. (39a).

17-Acetoxy-heptadecanol (4.4 g, 13.99 mmol), Ph$_3$P (4.4 g, 16.78 mmol) and imidazole (1.57 g, 23.08 mmol) were dissolved in the mixture of CH$_2$Cl$_2$ (40 ml) and benzene (20 ml). The mixture was cooled to 0° C. and solid I$_2$ (4.26 g, 16.78 mmol) was added in one portion. The mixture was stirred at 0° C. for 15 min and at room temperature for 30 min. The reaction was quenched by the addition of EtOH (1.5 ml), stirred for 10 min at room temperature, diluted with hexane-EtOAc (1:1) mixture and washed with aqueous NaHCO$_3$—Na$_2$S$_2$O$_3$ solution. The organic extract was dried Na$_2$SO$_4$ and evaporated. Residue was stirred with hexane (300 ml) for 20 min and the suspension was filtered to remove Ph$_3$PO. The filtrate was evaporated and the residue was chromatographed on silica gel in hexane-EtOAc (98:2) to give 17-acetoxy-heptadecyl iodide (5.89 g, 99%).

Synthesis of 18-(p-Iodophenyl)octadecyl acetate (42).

Zinc powder (340 mg, 5.21 mmol) was dried in a 25-ml flask under high vacuum at 70° C. for 30 min, then DMA (1 ml) and I$_2$ (44 mg, 0.17 mmol) were added. After 10 min, a solution of 17-acetoxy-heptadecyl iodide 39a (1.473 g, 3.47 mmol) in DMA (5 ml) was added. The mixture was stirred at 60-70° C. for 10 h and cooled to room temperature. A solution of the organozinc reagent was transferred via cannula into a 25 ml round bottom flask equipped with the stir bar. The flask with organozinc solution 41 was immersed in an ice bath. In a 10-ml round bottom flask, NiCl$_2$.glyme (76 mg, 0.347 mmol) and (R)-(i-Pr)-Pybox (or (S)-(i-Pr)-Pybox) (136 mg, 0.45 mmol) were dissolved in DMA (2 ml), then a solution of p-iodobenzyl bromide 5 (1.55 g, 5.21 mmol) in DMA (3 ml) was added. The solution of NiCl$_2$-Pybox catalyst and p-iodobenzyl bromide was added to the solution of organozinc reagent 41 at 0° C. within 2-3 min. The reaction mixture was stirred at 0° C. for 30 min and at room temperature for 12-24 h. The reaction was quenched by addition of aqueous NH$_4$Cl, extracted with EtOAc, the extract was dried over Na$_2$SO$_4$ and evaporated. The crude product was purified by silica gel chromatography in hexane-ether (98:2) to yield the product (1.58 g, 88%).

Synthesis of 18-(p-Iodophenyl)octadecanol (12) from (42).

18-(p-Iodophenyl)octadecyl acetate 42 (1.55 g, 3.01 mmol) was dissolved in THF (10 ml), MeOH (5 ml) and a solution of NaOH (240 mg, 6.03 mmol) in H$_2$O (1 ml) was added. The reaction mixture was stirred at room temperature for 2 h, quenched with aqueous NaHCO$_3$ solution and extracted with EtOAc. The extract was dried over Na$_2$SO$_4$ and evaporated. Silica gel chromatography in hexane-EtOAc (95:5, 90:10) gave the product, 1.36 g (95%).

In general, the choice of coupling partners may depend on commercial availability of starting materials since $C_{18}$ alkyl chain can be assembled from many different fragments (more than two or three). In addition to alkyl bromides, alkyl iodides can be used for generation of organozinc reagents. p-Iodobenzyl chloride or iodide can be used instead of p-iodobenzyl bromide 5. As described by G. Fu, Ni(COD)$_2$, NiCl$_2$.glyme or NiBr$_2$.diglyme can be used as Ni(II) sources, and compounds 71, 72, 73, 74 and 75 in any enantiomeric form can serve as ligands (Zhou J R, Fu G C. *J. Am. Chem. Soc.* 2003; 125: 14726-14727; Fischer C, Fu G C. *J. Am. Chem. Soc.* 2005; 127: 4594-4595; Arp F O, Fu G C. *J. Am. Chem. Soc.* 2005; 127: 10482-10483; Son S S, Fu G C. *J. Am. Chem. Soc.* 2008; 130: 2756-2757). N,N-Dimethylacetamide (DMA), N-methyl-2-pyrrolidone (NMP) or 1,3-dimethyl-2-imidazolidinone (DMI) in combination with THF can be used as solvents for cross-coupling reaction.

Another approach is shown in SCHEME III. It can be described as $C_{16}+IPhC_2=IPhC_{18}$. The $C_{16}$ fragment 43 originates from relatively inexpensive 16-hexadecanolactone 31. Lactone cleavage with trimethylsilyl iodide in the presence of ethanol results in ethyl 16-iodohexadecanoate 43. Iodoester 43 is coupled with organozinc reagent 44 made from 2-(p-iodophenyl)ethyl bromide to give ester 37 which has all 18 carbons chain required for NM404. Ester 37 is converted into 18-(p-iodophenyl)octadecanol 12 in two steps as shown in SCHEME III.

SCHEME III:

Synthesis of 43 is based on procedures well-known in the art. See, for example, Canadian Patent No. CA 2 339 495.

Final conversion of ω-(iodophenyl)-alkyl alcohol into its corresponding phosphocholine follows. SCHEME IV illustrates one method for converting 18-(p-iodophenyl)octadecanol 12 into 18-(β-iodophenyl)-octadecyl phosphocholine 1 (NM404). This procedure is also described in the literature. (Pinchuk A N, Rampy M A, Longino L A, Skinner R W S, Gross M D, Weichert J P, Counsell R E. *J. Med. Chem.* 2006; 49: 2155-2165).

SCHEME IV:

EXAMPLE 2

Cross-Coupling of Alkyl Zinc Reagents with Alkyl Halides

In the synthetic scheme illustrated in SCHEME V, the inventors disclose the synthesis of PLEs based on cross-coupling of alkyl zinc reagents with alkyl halides catalyzed by Ni(II)-i-Pr-Pybox and/or Pd-PEPPSI-IPr complexes. Reaction conditions were optimized for various combinations of alkyl halides and organozinc reagents allowing the production of desired PLE analogs in multigram quantities. In these reactions, the chain elongation sequence can be abbreviated as $C_6+C_{11}+PhC_1=IPHC_{18}$

SCHEME V:

Methods

Synthesis of Tetrahydro-2-(17-acetoxyheptadecyloxy)-2H-pyran (39).

In a 50-ml flask, zinc powder (98 mg, 1.5 mmol) was dried at 70° C. under high vacuum for 30 min. After back-filling with nitrogen, DMI (25 ml) was added followed by solid $I_2$ (380 mg, 1.53 mmol) for Zn activation. The iodine color disappeared after stirring for 5 min. Neat 6-bromohexyl acetate (6.83 g, 30.61 mmol) was added and the mixture was stirred at 65-80° C. for 2-14 h, cooled to the room temperature, excess zinc was allowed to settle, and the organozinc solution 46 was transferred via cannula into a solution of anhydrous LiBr (5.32 g, 61, 23 mmol) in THF (50 ml). The solution of organozinc reagent in DMI-THF mixture was cooled to 0° C. and solution of PEPPSI-IPr (130 mg, 0.191 mmol) in DMI (3 ml) was added followed by a rapid addition of neat $Br(CH_2)_{11}OTHP$ 47 (6.42 g, 19.13 mmol). The cooling bath was removed and the reaction mixture was stirred at room temperature for 9 h. Reaction mixture was quenched with aqueous $NH_4Cl$ solution (250 ml) and extracted with EtOAc (250 ml). The extract was washed with aqueous $NH_4Cl$ solution, dried over $Na_2SO_4$ and concentrated under reduced pressure. The crude product was chromatographed on silica gel in hexane-EtOAc (97:3) to give the compound 39 (7.09 g, 93%).

As shown above in SCHEME V, by starting with alkyl zinc reagent 46 and alkyl halide reagent 47, C17 fragment 39 is produced using Ni(II)-i-Pr-Pybox or PEPPSI-IPr complexes as catalysts. Conversion of 18-(p-iodophenyl)octadecyl acetate 42 to 18-(p-iodophenyl)octadecanol 12 is achieved in one step using acetate hydrolysis by sodium hydroxide while conversion of the ethyl ester 37, shown in SCHEMES III and V is a two step process, first by hydrolysis 37 with NaOH and second by the acid reduction with borane.

FIG. 4A, shows the reduction of 42 to 12 while FIG. 4B shows the hydrolysis of 37 followed by reduction to 12. FIG. 4C shows the conversion of 1 to the boronic ester thereby allowing isotope labeling. When the method comprises alkyl chain synthesis as described in SCHEMES II and V and FIGS. 5 and 6, alkyl chain synthesis is followed by attachment of the p-Iodophenyl group as shown in FIG. 7.

EXAMPLE 3

Attachment of the p-Iodophenyl Group

As discussed above, when they PLE synthesis method proceeds via a chain elongation process summarized as: $IPhC_1+C_{11}+C_6=IPhC_{18}$, $C_6+C_{11}+IPhC_1=IPhC_{18}$, or $C_{16}+IPhC_2=IPhC_{18}$. The process is followed by attachment of the p-iodophenyl group as shown in SCHEME VI and VII and further illustrated in FIG. 7.

SCHEME VI:

SCHEME VII:

Another combination of alkyl halides and organozinc reagents is shown in Scheme VIII.

SCHEME VIII:

Methods

Synthesis of Ethyl 17-(tetrahydropyran-2-yl-oxy)-heptadecanoate (78).

Method 1. From (38) and (76). Zinc powder (166 mg, 2.55 mmol) was dried at 70° C. for 30 min in a sealed tube, then DMA (2.5 ml) and solid 12 (22 mg, 0.09 mmol) were added. After stirring for 10 min, neat ethyl 11-bromoundecanoate (500 mg, 1.7 mmol) was added and the reaction mixture was stirred in the sealed tube for 10 h at 80° C. In a 10-ml flask, $NiCl_2$-glyme (29 mg, 0.13 mmol) and (R)-(i-Pr)-Pybox (or (S)-(i-Pr)-Pybox) (51 mg, 0.17 mmol) were dissolved in DMA (1.5 ml) and THF (0.5 ml), then neat $I(CH_2)_6OTHP$ 38 (410 mg, 1.31 mmol) was added. This mixture was cooled to 0° C. and organozinc solution 76 was added via cannula. The reaction mixture was allowed to warm to the room temperature over period of 12 h and stirred at room temperature for additional 12 h. The reaction was quenched by addition of aqueous $NH_4Cl$, extracted with EtOAc, the extract was dried over $Na_2SO_4$ and evaporated. The crude product was purified by silica gel chromatography in hexane-EtOAc (98:2, 97:3, 96:4) to afford the product ethyl 17-(tetrahydropyran-2-yl-oxy)-heptadecanoate 78 (369 mg, 71%).

Method 2. From (77) and (36). Zinc powder (342 mg, 5.27 mmol) was dried at 70° C. for 30 min in a sealed tube, then DMA (2 ml) and solid 12 (45 mg, 0.18 mmol) were added. After stirring for 10 min, neat ethyl 6-bromohexanoate (0.63 ml, 3.52 mmol) was added and the reaction mixture was stirred in the sealed tube for 10 h at 75° C. In a 10-ml flask, $NiCl_2$-glyme (52 mg, 0.23 mmol) and (R)-(i-Pr)-Pybox (or (S)-(i-Pr)-Pybox) (92 mg, 0.31 mmol) were dissolved in DMA (1.5 ml), cooled to 0° C. and solution of $I(CH_2)_{11}OTHP$ 77 (896 mg, 2.34 mmol) in DMA (0.5 ml) was added. Then the solution of organozinc reagent 36 was added. The reaction mixture was stirred at 0° C. for 6 h and at room temperature for 6 h, then quenched by addition of aqueous $NH_4Cl$, extracted with EtOAc, extract was dried over $Na_2SO_4$ and evaporated. The crude product was purified as in Method 1 to give compound 78 (888 mg, 95%).

Synthesis of Ethyl 17-hydroxy-heptadecanoate (79).

Ethyl 17-(tetrahydropyran-2-yl-oxy)-heptadecanoate 78 (365 mg, 0.916 mmol) and PPTS (12 mg, 0.046 mmol) were dissolved in abs. EtOH (6 ml) and the reaction mixture was stirred at 45° C. for 10 h. Reaction mixture was diluted with EtOAc and washed with $H_2O$. The extract was dried over $Na_2SO_4$ and evaporated. The residue was purified by silica gel chromatography in hexane-EtOAc (95:5, 90:10) to yield the product 79 (266 mg, 92%).

Synthesis of Ethyl 17-iodo-heptadecanoate (80).

Ethyl 17-hydroxy-heptadecanoate 79 (264 mg, 0.84 mmol), $Ph_3P$ (262 mg, 1 mmol) and imidazole (94 mg, 1.39 mmol) were dissolved in the mixture of $CH_2Cl_2$ (3 ml) and benzene (3 ml) and cooled to 0° C. Solid 12 (254 mg, 1 mmol) was added and the reaction mixture was stirred at 0° C. for 40 min. The reaction mixture was quenched by addition of MeOH (0.5 ml), diluted with EtOAc and washed with the aqueous $NaHCO_3$—$Na_2S_2O_3$ solution, dried over $Na_2SO_4$ and evaporated. Chromatography in hexane-EtOAc (97:3) afforded the product 80 (321 mg, 90%).

Synthesis of Ethyl 18-(p-iodophenyl)octadecanoate (37) from (80).

Zinc powder (70 mg, 1.06 mmol) was dried at 70° C. for 30 min in a sealed tube, then DMA (0.4 ml) and solid 12 (9 mg, 0.04 mmol) were added. After stirring for 10 min, a solution of ethyl 17-iodo-heptadecanoate 80 (300 mg, 0.71 mmol) in DMA (1.5 ml) was added and the reaction mixture was stirred in the sealed tube for 11 h at 70° C. In a 10-ml flask, $Ni(COD)_2$ (10 mg, 0.04 mmol), (R)-(s-Bu)-Pybox (or (S)-(s-Bu)-Pybox) (23 mg, 0.07 mmol) and p-iodobenzyl chloride 82 (252 mg, 1 mmol) were dissolved in DMA (1.5 ml), then organozinc solution 81 was added via cannula. The mixture was stirred at room temperature for 15 h, and the reaction was quenched by addition of aqueous $NH_4Cl$, extracted with EtOAc, the extract was dried over $Na_2SO_4$ and evaporated. Chromatography of the crude product in hexane-ether (97:3) yielded the compound 37 (276 mg, 76%).

EXAMPLE 4

Exemplary Synthesis of High Specific Activity NM404

In the synthesis of high specific activity NM404 the inventors approach was based on the use of organoboron compounds as precursors to radiohalogenated pharmaceuticals. There are several methods for labeling molecules with radiohalogens via organometallic intermediates containing mercury, thallium, boron, silicon, germanium and lead (Kabalka, G. W.; Varma, R. S. The synthesis of radiolabeled compounds via organometallic intermediates. *Tetrahedron* 1989, 45, 6601-6621).

Another aspect of the invention is illustrated in Schemes IX-XIII.

Scheme IX.

SCHEME IX:

In various exemplary embodiments, the PdCl$_2$ catalyst used in SCHEME IX has the structure shown in formula IV:

IV

In the case of the neopentyl glycol ester, the neopentyl moiety did not survive the conditions of chromatography in the CHCl$_3$-MeOH—H$_2$O solvent system, and the product was obtained as a boronic acid 44. A pinacol ester was more stable towards hydrolysis, and pinacol boronic ester 45 could be isolated in the reaction of NM404 with bis-(pinacolato) diboron. This reaction is shown in SCHEME X. Pinacol ester 45 was also obtained by esterification of borono-NM404 (44) with pinacol, and this two steps procedure is a preferred method since the product has higher purity (SCHEME XI). Conditions of cross-coupling reaction were optimized and the amount of catalyst PdCl$_2$ (dppf) was in the range of 1-5%.

SCHEME X:

45

SCHEME XI:

44

45

In a cold run, both borono-NM404 (44) and pinacol boronate of NM404 (45) were converted back to NM404 (1) by reaction with NaI in the presence of chloramine-T (10-20 mg scale) in about 90% yield (SCHEME XII).

SCHEME XII:

Dihydroxyboryl compound 44 was converted into $^{125}$I-NM404 according to SCHEME XIII. Chloramine-T served as an oxidant and the solvent was the mixture of ethanol and 0.1 N hydrochloric acid. The radiochemical yield was in the range of 40-50%, the radiochemical purity was 92-98%.

SCHEME XIII:

The methods illustrated in SCHEMES IX-XIII, can be summarized as follows:
(a) coupling an ester of diboron with a PLE or APC analog in the presence of a catalyst to result in a boronic acid or ester PLE or APC analog;
(b) optionally, esterifying the boronic acid of the PLE analog with 1,2-or 1,3-diols to result in the boronic esters of PLE or APC analog to step (a); and
(c) optionally, reacting the boronic acid or ester of PLE or APC analog of step (a) or (b) with sodium radiohalide, in the presence of an oxidant to result in a high specific activity radiohalogenated PLE or APC analog.

In some versions, the coupling reaction of step (a) is carried out with methanol as a solvent at temperatures of about 15-70° C. in the presence of a Pd catalyst. In still other versions, the in step (c) the oxidant is selected from the group consisting of: dichloramine-T; chloramine-B, dichloramine-B; iodogen, iodogen coated tubes, iodobeads, N-chlorosuccinimide; hydrogen peroxide, peracetic acid, m-chloro-perbenzoic acid and peroxidase. In other embodiments, the catalyst is:

III wherein R is selected from the group consisting of: i-Pr: i-Pr-Pybox, s-Bu: s-Bu-Pybox, Ph: Ph-Pybox and H: Pybox. In some preferred embodiments, the invention includes an intermediate in the synthesis having the structure:

V

In this embodiment, M is selected from the group consisting of Li, Na, K, Cs and Rb. Further, it should be appreciated that, where the boronic ester of the PLE or APC analog is the desired product. Optionally, the method may end at step (b) thereby achieving the synthesis of a desired boronic ester of the PLE or APC analog that may be used, for example, with boron neutron capture therapy to treat cancer.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:
1. A method of synthesizing a phospholipid ether (PLE) analog or an alkyl phosphocholine (APC) analog comprising by the cross-coupling of an organo zinc reagent with an alkyl halide reagent comprising the steps of:

a) coupling an alkyl organo metallic with an alkyl iodide in the presence of an Ni(II)-Pybox or Pd-PEPPSI catalyst;
b) attaching an iodophenyl group in the presence of an Ni(II)-Pybox catalyst to yield an iodophenyl alcohol; and
c) converting the iodophenyl alcohol to an iodophenyl phosphocholine using an ethylene chlorophosphate and trimethylamine;

wherein an alkyl phosphocholine or a phospholipid ether is synthesized.

2. The method of claim 1, wherein the phospholipid ether analog has the formula:

where X is selected from the group consisting of radioactive isotopes of halogen; n is an integer between 8 and 30; and Y is selected from the group comprising $NH_2$, $NR_2$, and $NR_3$, wherein R is an alkyl or arylalkyl substituent or:

where X is a radioactive isotope of halogen; n is an integer between 8 and 30; Y is selected from the group consisting of H, OH, COOH, COOR and OR, and Z is selected from the group consisting of $NH_2$, $NR_2$, and $NR_3$, wherein R is an alkyl or arylalkyl substituent.

3. The PLE analog of claim 2, wherein X is selected from the group of radioactive halogen isotopes consisting of $^{18}F$, $^{36}Cl$, $^{76}Br$, $^{77}Br$, $^{82}Br$, $^{122}I$, $^{123}I$, $^{124}I$, $^{125}I$, $^{131}I$, $^{211}At$ and combinations thereof.

4. The method of claim 1, wherein an alkyl chain elongation process is: $IPhC_1 + C_{11} + C_6 = IPhC_{18}$, $C_6 + C_{11} + IPhC_1 = IPhC_{18}$ or $C_{16} + IPhC_2 = IPhC_{18}$.

5. The method of claim 1, wherein in step b, the catalyst is:

wherein R is selected from the group consisting of: i-Pr: i-Pr-Pybox; s-Bu: s-Bu-Pybox; Ph: Ph-Pybox; H: Pybox; $BnCH_2$: $BnCH_2$-Pybox; or 6. The method of claim 1, further including synthesizing a high specific activity phospholipid ether (PLE) analog, comprising the steps of:
 (a) coupling an ester of diboron with a PLE or APC analog in the presence of a catalyst to result in a boronic acid or ester PLE or APC analog;
 (b) optionally, esterifying the boronic acid of the PLE analog with 1,2- or 1,3-diols to result in the boronic esters of PLE or APC analog to step (a); and
 (c) optionally, reacting the boronic acid or ester of PLE or APC analog of step (a) or (b) with sodium radiohalide, in the presence of an oxidant to result in a high specific activity radiohalogenated PLE or APC analog.

7. The method of claim 5, wherein the coupling reaction of step (a) is carried out with methanol as a solvent at temperature of about 15-70° C. in the presence of a Pd catalyst.

8. The method of claim 6, wherein the catalyst has the formula:

9. The method of claim 5, wherein in step (c) the oxidant is selected from the group consisting of: dichloramine-T, chloramine-B, dichloramine-B, iodogen, iodogen coated tubes, iodobeads, N-chlorosuccinimide, hydrogen peroxide, peracetic acid, m-chloro-perbenzoic acid and peroxidase.

10. The method of claim 5, wherein the synthesis of the high specific activity PLE analog proceeds through an intermediate having the structure:

where M is selected from the group consisting of Li, Na, K, Cs and Rb.

UNITED STATES PATENT AND TRADEMARK OFFICE
CERTIFICATE OF CORRECTION

| | | |
|---|---|---|
| PATENT NO. | : 7,893,286 B2 | |
| APPLICATION NO. | : 12/156287 | |
| DATED | : February 22, 2011 | |
| INVENTOR(S) | : Anatoly Pinchuk, Jamey P. Weichert and Marc Longino | |

It is certified that error appears in the above-identified patent and that said Letters Patent is hereby corrected as shown below:

In The Specifications:
In Column 8, line 37, please delete the word "by"

In The Claims:
In Claim 1, column 24, line 66, please delete the word "by"

Signed and Sealed this
Twenty-fourth Day of May, 2011

David J. Kappos
*Director of the United States Patent and Trademark Office*